(12) United States Patent
Gilmartin et al.

(10) Patent No.: US 8,366,970 B2
(45) Date of Patent: Feb. 5, 2013

(54) METHOD FOR TREATING A CARBON ALLOTROPE

(75) Inventors: Brian Gilmartin, Williamsville, NY (US); Jin Wu, Pittsford, NY (US); Liang-Bih Lin, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 244 days.

(21) Appl. No.: 12/832,700

(22) Filed: Jul. 8, 2010

(65) Prior Publication Data
US 2012/0010337 A1 Jan. 12, 2012

(51) Int. Cl.
*H01B 1/20* (2006.01)
(52) U.S. Cl. ............... 252/511; 252/502; 423/449.2; 423/449.6; 428/403; 428/405; 524/424
(58) Field of Classification Search ............... None
See application file for complete search history.

(56) References Cited

U.S. PATENT DOCUMENTS

| | | | |
|---|---|---|---|
| 6,248,808 B1 * | 6/2001 | Sone et al. | 523/215 |
| 6,652,641 B2 * | 11/2003 | Kawazura | 106/475 |
| 6,852,794 B2 | 2/2005 | Puhala et al. | |
| 7,468,231 B2 | 12/2008 | Lin et al. | |
| 8,096,649 B2 | 1/2012 | Sambhy et al. | |
| 8,226,207 B2 | 7/2012 | Kovacs et al. | |
| 2008/0213322 A1 * | 9/2008 | Birman et al. | 424/401 |
| 2009/0137731 A1 * | 5/2009 | Sekiyama et al. | 524/588 |
| 2010/0035070 A1 | 2/2010 | Moorlag et al. | |
| 2010/0071818 A1 * | 3/2010 | Hergenrother et al. | 152/209.1 |
| 2010/0159375 A1 | 6/2010 | Zhou et al. | |
| 2010/0159376 A1 | 6/2010 | Zhou et al. | |
| 2011/0045186 A1 | 2/2011 | Gervasi et al. | |
| 2011/0045305 A1 | 2/2011 | Gilmartin et al. | |
| 2011/0157276 A1 | 6/2011 | Zhao et al. | |
| 2011/0157277 A1 | 6/2011 | Zhao et al. | |
| 2011/0157278 A1 | 6/2011 | Gulvin et al. | |

OTHER PUBLICATIONS

"Synthesis and Applications of Functionalized Sllsesquioxane Particles Attached to Organic and Inorganic Matrices" authored by Gushikem and published in Pure and Applied Chemistry (2008), 80(7), 1593-1611.*
Abstract for FR 2925507 (Jun. 2009).*
Advisory Action mailed Jun. 21, 2012 in U. S. Patent Publication 2011-0045305, 4 pages.
Final Rejection mailed Apr. 13, 2012 in U. S. Patent Publication 2011-0045305, 30 pages.
Non-Final Rejection mailed Aug. 19, 2011 in U. S. Patent Publication 2011-0045305, 30 pages.

* cited by examiner

*Primary Examiner* — Marc Zimmer
(74) *Attorney, Agent, or Firm* — Marylou J. Lavoie

(57) ABSTRACT

A method for treating a carbon allotrope including providing a carbon allotrope selected from the group consisting of carbon black, amorphous carbon, glassy carbon, graphite, graphene, fullerenes, or a mixture thereof; surface treating the carbon allotrope by coupling the carbon allotrope with a polyhedral oligomeric silsesquioxane. Also described is a surface treated carbon allotrope having a polyhedral oligomeric silsesquioxane coupled to the surface of the carbon allotrope. Also described is a coating composite for imaging components including a film forming resin; and a plurality of polyhedral oligomeric silsesquioxane surface treated carbon allotrope particles substantially uniformly dispersed in the film forming resin, and imaging components including the coating composite.

20 Claims, 1 Drawing Sheet

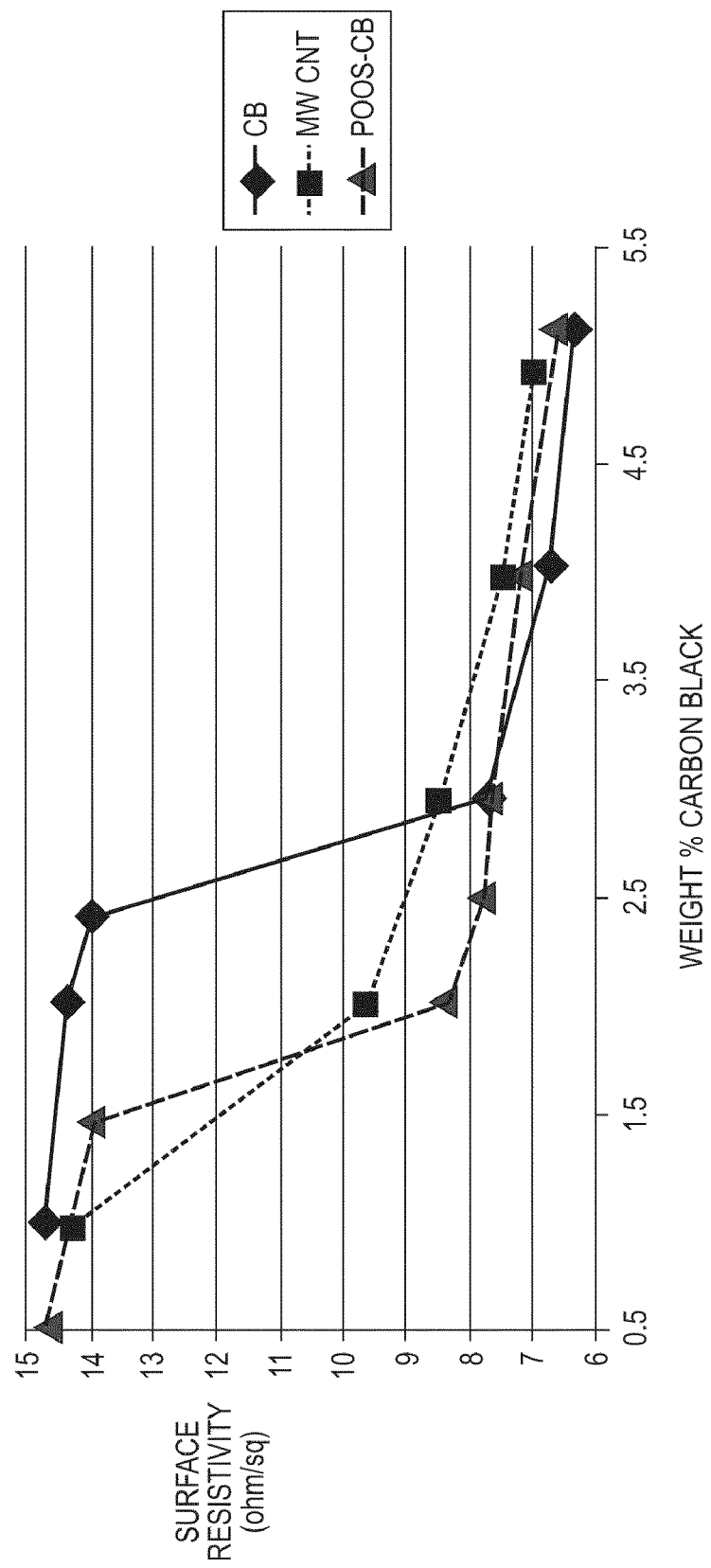

METHOD FOR TREATING A CARBON ALLOTROPE

RELATED APPLICATIONS

Commonly assigned U.S. patent Ser. No. 12/546,055, entitled "Treatment of Carbon Black With A Fluorosilane"), filed Aug. 24, 2009, which is hereby incorporated by reference herein in its entirety, describes coating composites for imaging members, imaging members, and apparatuses for forming an image. In accordance with various embodiments, there is a coating composite for imaging components. The coating composite can include a film forming resin and a plurality of surface treated carbon black particles substantially uniformly dispersed in the film forming resin, wherein each of the plurality of surface treated carbon black particles includes one or more fluorosilanes bonded to a surface of the carbon black particle.

BACKGROUND

Disclosed herein is a method for treating carbon black, and more specifically, a method for surface treating carbon black with a polyhedral oligomeric silsesquioxane, and a carbon black material prepared by the method.

As one of the top 50 industrial chemicals produced worldwide, carbon black is used in a number of different industrial applications. Approximately 8.1 million tons of carbon black is produced annually, and it is the most commonly used conductive agent used in plastics, coatings, toners and printing inks. Although there is great demand for carbon black in materials production, it suffers from a percolation threshold which can greatly affect the conductivity of the material. The percolation threshold relates subtle changes in carbon black concentration to a dramatic change in conductivity. Due to this effect, materials can go from being conductive to being resistive by varying the concentration of carbon black ever so slightly, for example, less than 1 weight percent variation. For electrically conductive materials, a significant amount of carbon black may be required in order to achieve the conductivity necessary for a given material, which can diminish the strength of the materials. For materials which require a specific conductivity, such as intermediate transfer belts and bias charge rollers, this can be problematic from an electronic and mechanical standpoint. There are many types of carbon blacks of various particle size and physical properties, which offer different ranges of conductivity. However, each of these carbon blacks typically suffers from the same percolation issue.

Currently available methods for preparing carbon black are suitable for their intended purposes. However, a need remains for an improved system and method that is suitable for treating carbon black. A need also remains for an improved method for treating carbon black materials which can tailor the conductivity in the range difficult to achieve by pure, untreated carbon black. Further, a need remains for a method for treating carbon black to control the percolation threshold and enable use of lower concentrations of carbon black. Still further, a need remains for an improved method for treating carbon black materials which can tailor the conductivity in the range previously available only with more expensive materials.

The appropriate components and process aspects of the each of the foregoing U.S. Patents and Patent Publications may be selected for the present disclosure in embodiments thereof. Further, throughout this application, various publications, patents, and published patent applications are referred to by an identifying citation. The disclosures of the publications, patents, and published patent applications referenced in this application are hereby incorporated by reference into the present disclosure to more fully describe the state of the art to which this invention pertains.

SUMMARY

Described is a method for treating a carbon allotrope comprising: providing a carbon allotrope selected from the group consisting of carbon black, amorphous carbon, glassy carbon, graphite, graphene, fullerenes, or a mixture thereof; and surface treating the carbon allotrope by coupling the carbon allotrope with a polyhedral oligomeric silsesquioxane, wherein the polyhedral oligomeric silsesquioxane comprises a compound of the formula

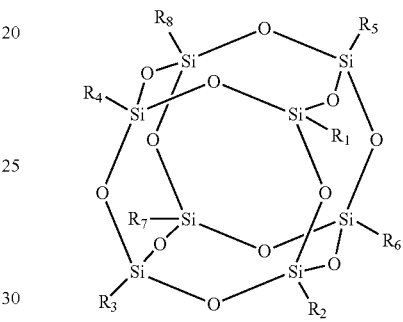

wherein $R_1$, $R_2$, $R_3$, $R_4$, $R_5$, $R_6$, $R_7$, and $R_8$ are each, independently of the other, selected from a fluorine-substituted group comprising (a) alkyl, including linear, branched, saturated, unsaturated, cyclic, acyclic, substituted, and unsubstituted alkyl groups, and wherein hetero atoms may optionally be present in the alkyl group; (b) aryl, including substituted and unsubstituted aryl groups, and wherein hetero atoms may optionally be present in the aryl group; (c) arylalkyl, including unsubstituted and substituted arylalkyl groups, wherein the alkyl portion of the arylalkyl group can be linear, branched, saturated, unsaturated, cyclic, or acyclic, and wherein hetero atoms may optionally be present in either or both of the alkyl portion and the aryl portion of the arylalkyl group; (d) alkylaryl, including unsubstituted and substituted alkylaryl groups, wherein the alkyl portion of the alkylaryl group can be linear, branched, saturated, unsaturated, cyclic, or acyclic, and wherein hetero atoms may optionally be present in either or both of the alkyl portion and the aryl portion of the alkylaryl group; (e) siloxyl, including linear, branched, cyclic, acyclic, substituted, and unsubstituted, siloxyl groups, and wherein hetero atoms may optionally be present; (f) silyl, including linear, branched, cyclic, acyclic, substituted, and unsubstituted, silyl groups, and wherein hetero atoms may optionally be present; (g) silane, including linear, branched, cyclic, acyclic, substituted, and unsubstituted, silane groups, and wherein hetero atoms may optionally be present; and (h) a functional group selected from hydroxyl, amine, carboxylic acid, epoxide, fluoroalkyl, halide, imide, acrylate, methacrylate, nitrile, sulfonate, thiol, silanol, and combinations thereof, wherein two or more R groups can be joined together to form a ring.

Also described is a surface treated carbon allotrope comprising a carbon allotrope selected from the group consisting of carbon black, amorphous carbon, glassy carbon, graphite, graphene, fullerenes, or a mixture thereof, having a polyhedral oligomeric silsesquioxane coupled to the surface of the carbon allotrope, wherein the polyhedral oligomeric silsesquioxane comprises a compound of the formula as described herein.

Also described is a coating composite for imaging components comprising a film forming resin; and polyhedral oligomeric silsesquioxane surface treated carbon allotrope substantially uniformly dispersed in the film forming resin, wherein the carbon allotrope is selected from the group consisting of carbon black, amorphous carbon, glassy carbon, graphite, graphene, fullerenes, or a mixture thereof, and wherein the polyhedral oligomeric silsesquioxane comprises a compound of the formula described herein.

Also described is an imaging component comprising a substrate; a coating composite disposed over the substrate, the coating composite comprising polyhedral oligomeric silsesquioxane surface treated carbon allotrope substantially uniformly dispersed in a film forming resin, wherein the carbon allotrope is selected from the group consisting of carbon black, amorphous carbon, glassy carbon, graphite, graphene, fullerenes, or a mixture thereof, and wherein the polyhedral oligomeric silsesquioxane comprises a compound of the formula as described herein.

BRIEF DESCRIPTION OF THE DRAWINGS

FIG. 1 is a graph showing surface resistivity (y-axis) versus weight percent material for POSS-treated carbon black, untreated carbon black, and multi-walled carbon nanotubes.

DETAILED DESCRIPTION

The present disclosure encompasses a method for tailoring carbon allotropes, in embodiments, carbon black, amorphous carbon, glassy carbon, graphite, graphene, fullerenes, and the like, and mixtures and combinations thereof. A method for tailoring the conductivity of carbon black by surface treatment of carbon black particles with polyhedral oligomeric silsesquioxanes (POSS) is described. As used herein, the terms "carbon black" and "carbon black particles" refer to colloidal particles that are produced by incomplete combustion or thermal decomposition of gaseous or liquid hydrocarbons under controlled conditions. In embodiments, the method comprises shifting the percolation threshold of carbon black by surface-treatment of carbon black particles with POSS. As used herein, percolation threshold refers to the effect caused by making subtle changes to the carbon black concentration of a material, which can lead to dramatic changes in the conductivity. In embodiments, surface treating carbon black herein comprises controlling the percolation threshold of carbon black by selective coupling of carbon black particles with a polyhedral oligomeric silsesquioxane. In specific embodiments, surface treating carbon black herein comprises controlling the percolation threshold of carbon black by selective coupling of carbon black particles with a polyhedral oligomeric silsesquioxane such that the percolation threshold of the carbon black is reduced from a percolation threshold of about 3 weight % for untreated carbon black to a percolation threshold of about 2 weight % for POSS surface treated carbon black.

Further, a POSS surface-treated carbon allotrope material, in embodiments, carbon black, is described. Films prepared with the present POSS surface treated carbon black can have a conductivity profile that is shifted from that of untreated carbon black. In embodiments, films prepared with the present POSS surface treated carbon black can have a conductivity profile that is the same as or similar to films prepared with multi-walled carbon nanotubes (MWCNTs).

The POSS surface-treated carbon black of the present disclosure can be prepared by any suitable or desired method. In embodiments, a method for surface treating carbon black comprises surface treating carbon black by coupling carbon black particles with a polyhedral oligomeric silsesquioxane. In further embodiments, surface treating carbon black comprises controlling the percolation threshold of carbon black by selective coupling of carbon black particles with a polyhedral oligomeric silsesquioxane. In still further embodiments, the method of surface treating carbon black comprises coupling carbon black particles with a polyhedral oligomeric silsesquioxane to enhance the conductivity of carbon black at low carbon black loading levels. In a specific embodiment, the method comprises coupling carbon black particles with a polyhedral oligomeric silsesquioxane to enhance the conductivity of carbon black at low carbon black loading levels, wherein a loading level of 2 weight % POSS surface treated carbon black provides a resistivity of $10^8$ Ω/square (ohm/square).

In embodiments, films prepared with the present POSS surface treated carbon black having a carbon black loading of from about 0.01 to about 50, or from about 0.05 to about 25, or from about 0.1 to about 10 percent by weight, based upon the total weight of the film, have a resistivity in the range from about $10^4$ to about $10^{15}$, or from about $10^5$ to about $10^{14}$, or from about $10^6$ to about $10^{13}$, or from about $10^8$ to about $10^9$ Ω/square. In a specific embodiment, films prepared with the present POSS surface treated carbon black having a carbon black loading of about 2 percent by weight based upon the total weight of the film having a resistivity in the range of from about $10^8$ to about $10^9$ Ω/square. By comparison, films prepared with untreated carbon black at film loadings of less than about 3 weight percent carbon black based upon the total weight of the film have exhibited a resistivity of greater than about $10^{14}$ Ω/square.

In further embodiments, surface treated carbon black herein has a conductivity profile that is the same as or similar to multi-walled carbon nanotubes. In a specific embodiment, a film having the present surface treated carbon black has a conductivity profile that is the same as or similar to multi-walled carbon nanotubes.

In embodiments, a method for surface treating carbon black herein comprises preparing a solution comprising POSS and a liquid; and addition of the POSS solution to a suspension comprising carbon black, a coupling agent, and a base.

Any suitable or desired liquid can be used for dissolving the POSS, providing that the POSS is soluble in the liquid. In embodiments, alcohols, ketones, esters, ethers, halogenated solvents, such as chlorinated solvents, nitrogen containing solvents and mixtures thereof can be selected. Specific examples of suitable liquids include acetone, methyl acetate, methyl ethyl ketone, tetrahydrofuran, cyclohexanone, ethyl acetate, N,N-dimethylformamide, dioctyl phthalate, toluene, xylene, benzene, dimethylsulfoxide, mixtures and combinations thereof, and the like. In embodiments, the liquid is an organic solvent, such as a halogen containing organic solvent. In a specific embodiment the liquid can comprise dichloromethane.

The POSS can be dissolved in the liquid by any suitable or desired method, such as by stirring in the solvent for about one hour at room temperature (i.e., about 25° C.). If desired or necessary, the POSS can be dissolved in the solvent at an elevated temperature of from about 40° C. to about 85° C., from about 50° C. to about 80° C., or from about 60° C. to about 70° C.

The POSS can be dissolved in the liquid in any suitable or desired amount. In embodiments, from about 0.001 to about 10, from about 0.05 to about 5, or from about 0.1 to about 2 weight percent POSS can be provided in the liquid, based upon the total weight of the POSS and the liquid.

Any suitable or desired carbon black can be selected herein. In embodiments, carbon black can comprise Vulcan® XC72 carbon black available from Cabot Corporation.

The POSS solution can be combined with carbon black. Optionally, the POSS solution can be combined with carbon black and a coupling agent. Optionally, the carbon black and coupling agent are provided in a dispersion, and the POSS solution can be added to the carbon black and coupling agent dispersion.

Any suitable or desired coupling agent can be selected. In embodiments, the coupling agent can be selected from the group consisting of carbodiimides, including diisopropylcarbodiimide (DIC) and the like, and triazoles, including 1-hydroxy-benzotriazole (HOBt), 1-hydroxy-7-aza-benzotriazole (HOAt), benzotriazol-1-yl-oxytripyrrolidinophosphonium hexafluorophosphate (PyBOP), (2-(7-aza-1H-benzotriazole-1-yl)-1,1,3,3-tetramethyluronium hexafluorophosphate) (HATU), (2-(1H-benzotriazole-1-yl)-1,1,3,3-tetramethyluronium hexafluorophosphate) (HBTU), (2-(6-chloro-1H-benzotriazole-1-yl)-1,1,3,3-tetramethylaminium hexafluorophosphate) (HCTU), (2-(1H-benzotriazole-1-yl)-1,1,3,3-tetramethyluronium tetrafluoroborate) (TBTU) and the like, and mixtures and combinations thereof, which can be combined with a base, including piperidine, piperizine, 1-hydroxypiperidine, tetrabutylammonium fluoride, 1,8-diazabicyclo[5.4.0]undec-7-ene and the like, and mixtures and combinations thereof. In specific embodiments, the coupling agent can comprise dicyclohexylcarbodiimide (DCC) with diisopropylethylamine (DIPEA).

In a specific embodiment of the method herein, the liquid comprises a halogenated organic solvent; the coupling agent is selected from the group consisting of carbodiimides, triazoles, or a mixture or combination thereof; and the base is selected from the group consisting of piperidine, piperizine, 1-hydroxypiperidine, tetrabutylammonium fluoride, 1,8-diazabicyclo[5.4.0]undec-7-ene, diisopropylethylamine (DIPEA), or a mixture or combination thereof.

The carbon black dispersion can be prepared by any suitable or desired method. In embodiments, the carbon black dispersion can be prepared by combining carbon black, a solvent, and a coupling agent with stirring.

Any suitable or desired solvent can be used for the carbon black dispersion including alcohols, ketones, esters, ethers, halogenated solvents, such as chlorinated solvents, nitrogen containing solvents and mixtures thereof can be selected. Specific examples of suitable solvents include acetone, methyl acetate, methyl ethyl ketone, tetrahydrofuran, cyclohexanone, ethyl acetate, N,N-dimethylformamide, dioctyl phthalate, toluene, xylene, benzene, dimethylsulfoxide, dodecane, and mixtures and combinations thereof. The solvent can be the same or different from the solvent used for the POSS solution.

In embodiments, the carbon black dispersion can be pretreated, such as by sonication. Ultrasonication can be in any suitable or desired intensity and duration selected in accordance with the specific type and volume of carbon black dispersion being prepared. In embodiments, the carbon black is sonicated at a frequency of from about 20 kHz to about 10 MHz for a period of from about 1 to about 30 minutes.

The POSS solution can be added to the carbon black dispersion, with stirring, for any suitable or desired amount of time, such as from about 1 to about 72, or from about 5 to about 24, or for about 18 hours.

The POSS surface treated carbon black particles can then be isolated, such as by centrifuge, washed, such as with methylene chloride, and dried under vacuum. Drying can be by any suitable or desired method. In embodiments, the carbon black particles can be dried under vacuum at room temperature (typically about 20 to 25° C.).

The present method for surface treatment of carbon black particles with polyhedral oligomeric silsesquioxanes (POSS) can be accomplished with any suitable or desired POSS material. POSS-carbon black coupling can comprise functional groups on the POSS binding to the carbon black surface. In embodiments, POSS and functional groups on the POSS can be selected to optimize POSS binding to the carbon black particles. In embodiments, the method for treating a carbon allotrope comprises providing a carbon allotrope selected from the group consisting of carbon black, amorphous carbon, glassy carbon, graphite, graphene, fullerenes, or a mixture thereof; and surface treating the carbon allotrope by coupling the carbon allotrope with a polyhedral oligomeric silsesquioxane, wherein the polyhedral oligomeric silsesquioxane comprises a compound of the formula

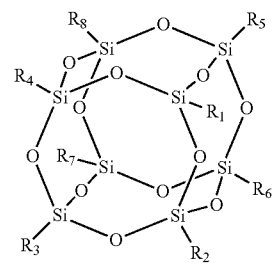

wherein $R_1$, $R_2$, $R_3$, $R_4$, $R_6$, $R_7$ and $R_8$ are each, independently of the other, selected from the group consisting of (a) alkyl, including linear, branched, saturated, unsaturated, cyclic, acyclic, substituted, and unsubstituted alkyl groups, and wherein hetero atoms may optionally be present in the alkyl group; (b) aryl, including substituted and unsubstituted aryl groups, and wherein hetero atoms may optionally be present in the aryl group; (c) arylalkyl, including unsubstituted and substituted arylalkyl groups, wherein the alkyl portion of the arylalkyl group can be linear, branched, saturated, unsaturated, cyclic, or acyclic, and wherein hetero atoms may optionally be present in either or both of the alkyl portion and the aryl portion of the arylalkyl group; (d) alkylaryl, including unsubstituted and substituted alkylaryl groups, wherein the alkyl portion of the alkylaryl group can be linear, branched, saturated, unsaturated, cyclic, or acyclic, and wherein hetero atoms may optionally be present in either or both of the alkyl portion and the aryl portion of the alkylaryl group; (e) siloxyl, including linear, branched, cyclic, acyclic, substituted, and unsubstituted, siloxyl groups, and wherein hetero atoms may optionally be present; (f) silyl, including linear, branched, cyclic, acyclic, substituted, and unsubstituted, silyl groups, and wherein hetero atoms may optionally be present; and wherein $R_5$ is selected from the group consisting of hydrogen, hydroxyl, amine, carboxylic acid, epoxide, halide, imide, acrylate, methacrylate, nitrile, sulfonate, thiol, silanol, dibromoethyl, norbornenylethyl, vinyl, chloropropyl, cyanopropyl, mercaptopropyl, aminopropyl, N-methylaminopropyl, propylammonium halide, allyl, chlorobenzyl, aminophenyl, N-phenylaminopropyl, norbornenyl, a group of the formula —(CH$_2$CH$_7$(OCH$_2$CH$_2$)$_m$OCH$_3$, wherein m is a number representing the number of repeat OCH$_2$CH$_2$ units, a group of the formula O—N$^+$(CH$_3$)$_4$,

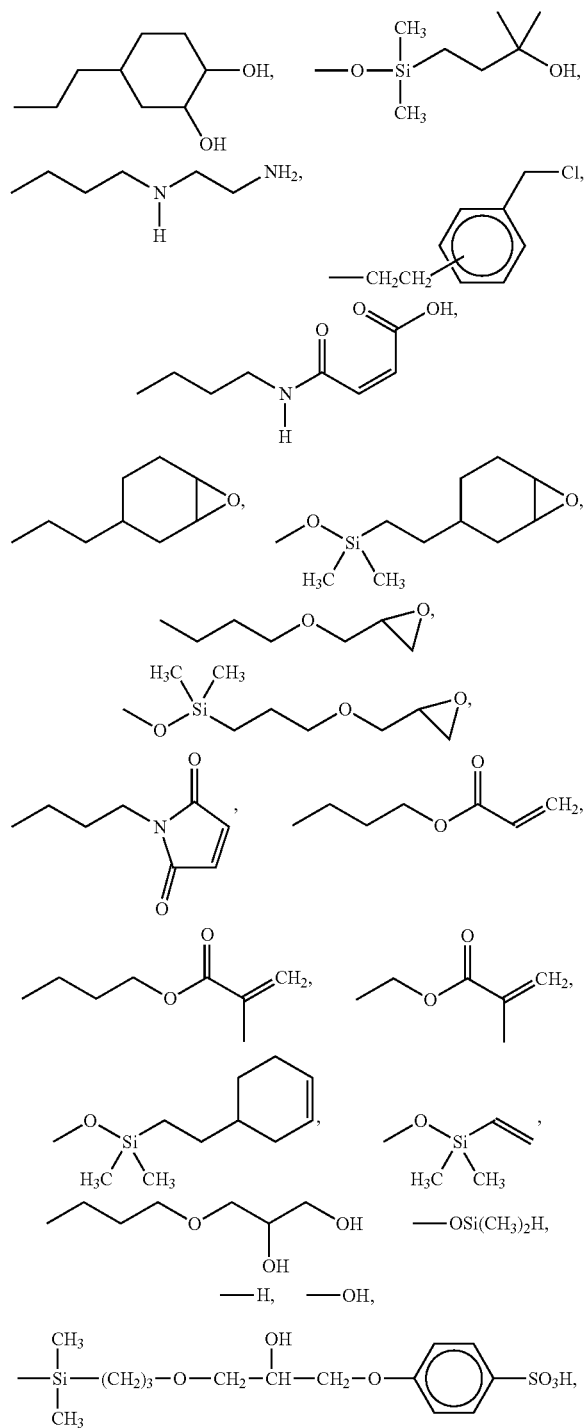

and combinations thereof. In embodiments, a polyhedral oligomeric silsesquioxane of the formula

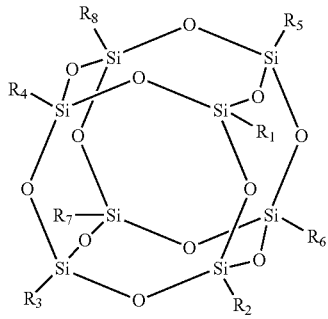

can be used, wherein R$_1$, R$_2$, R$_3$, R$_4$, R$_5$, R$_6$, R$_7$, and R$_8$ are each, independently of the other, selected from a fluorine-substituted group comprising (a) alkyl, including linear, branched, saturated, unsaturated, cyclic, acyclic, substituted, and unsubstituted alkyl groups, and wherein hetero atoms in addition to fluorine may optionally be present in the alkyl group; (b) aryl, including substituted and unsubstituted aryl groups, and wherein hetero atoms may optionally be present in the aryl group; (c) arylalkyl, including unsubstituted and substituted arylalkyl groups, wherein the alkyl portion of the arylalkyl group can be linear, branched, saturated, unsaturated, cyclic, or acyclic, and wherein hetero atoms may optionally be present in either or both of the alkyl portion and the aryl portion of the arylalkyl group; (d) alkylaryl, including unsubstituted and substituted alkylaryl groups, wherein the alkyl portion of the alkylaryl group can be linear, branched, saturated, unsaturated, cyclic, or acyclic, and wherein hetero atoms may optionally be present in either or both of the alkyl portion and the aryl portion of the alkylaryl group; (e) siloxyl, including linear, branched, cyclic, acyclic, substituted, and unsubstituted, siloxyl groups, and wherein hetero atoms may optionally be present; (f) silyl, including linear, branched, cyclic, acyclic, substituted, and unsubstituted, silyl groups, and wherein hetero atoms may optionally be present; (g) silane, including linear, branched, cyclic, acyclic, substituted, and unsubstituted, silane groups, and wherein hetero atoms may optionally be present; and (h) a functional group selected from hydroxyl, amine, carboxylic acid, epoxide, fluoroalkyl, halide, imide, acrylate, methacrylate, nitrile, sulfonate, thiol, silanol, and combinations thereof, wherein two or more R groups can be joined together to form a ring.

POSS materials have been implemented in the development of high performance materials in medical, aerospace, and commercial applications. POSS comprises thermally robust cages consisting of a silicon-oxygen core frame-work possessing alkyl functionality on the periphery. These molecules can be functionally tuned, are easily synthesized with inherent functionality, and are discreetly nano-sized. Furthermore, POSS compounds may possess a high degree of compatibility in blended polymers and can easily be covalently linked into a polymer backbone. The surface treatment of carbon black with POSS into polymers produces carbon black materials with improved properties, such as, but not limited to, improved mechanical strength, thermal and chemical resistance, lower surface energy, and ease of processing and controlling conductivity.

The method herein can comprise surface treating carbon black with POSS compounds having the generic formula (RSiO$_{1.5}$)$_n$ wherein R can be any of various hydrocarbons, siloxanes, functional groups, or the like, the R groups can be the same as or different from one another, and n is 6, 8, 10, 12, or higher. The silicon-oxygen framework in POSS molecules generally contains multiple ring structures in which each silicon atom is bound to one organic group and three oxygen atoms to form a fully condensed polycyclic structure. For example, when n is 8, structures as follows can form:

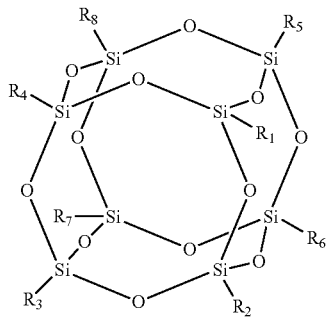

wherein $R_1$, $R_2$, $R_3$, $R_4$, $R_5$, $R_6$, $R_7$, and $R_8$ can be the same as or different from one another and are, for example, alkyl groups, including linear, branched, saturated, unsaturated, cyclic, acyclic, substituted, and unsubstituted alkyl groups, and wherein hetero atoms, such as oxygen, nitrogen, sulfur, silicon, phosphorus, boron, and the like may optionally be present in the alkyl group, having from about 1 to about 36, 6 to about 24, 6 to about 12, or 12 to about 18 carbons, although the number of carbon atoms can be outside of these ranges;

aryl groups, including substituted and unsubstituted aryl groups, and wherein hetero atoms, such as oxygen, nitrogen, sulfur, silicon, phosphorus, boron, and the like may optionally be present in the aryl group, having from about 6 to about 36, or about 6 to about 24, or about 12 to about 18 carbons atoms, although the number of carbon atoms can be outside of these ranges;

arylalkyl groups, including unsubstituted and substituted arylalkyl groups, wherein the alkyl portion of the arylalkyl group can be linear, branched, saturated, unsaturated, cyclic, and/or acyclic, and wherein hetero atoms, such as oxygen, nitrogen, sulfur, silicon, phosphorus, boron, and the like either may optionally be present in either or both of the alkyl portion and the aryl portion of the arylalkyl group, having from about 6 to about 36, or from about 7 to about 36, or from about 12 to about 18 carbon atoms, although the number of carbon atoms can be outside of these ranges, such as benzyl and the like;

alkylaryl groups, including unsubstituted and substituted alkylaryl groups, wherein the alkyl portion of the alkylaryl group can be linear, branched, saturated, unsaturated, cyclic, and/or acyclic, and wherein hetero atoms, such as oxygen, nitrogen, sulfur, silicon, phosphorus, boron, and the like either may optionally be present in either or both of the alkyl portion and the aryl portion of the alkylaryl group, having from about 6 to about 36, or from about 7 to about 36, or from about 12 to about 18 carbon atoms, although the number of carbon atoms can be outside of these ranges, such as tolyl and the like;

siloxyl, silyl, and silane groups, including those that are linear, branched, cyclic, acyclic, substituted, and unsubstituted, and wherein hetero atoms, such as oxygen, nitrogen, sulfur, phosphorus, boron, and the like may optionally be present, having from about 1 to about 12 or from about 3 to about 6 silicon atoms, although the number of silicon atoms can be outside of these ranges, wherein the substituents on the alkyl, aryl, arylalkyl, alkylaryl, siloxyl, silyl, and silane groups can be (but are not limited to) hydroxy groups, halogen atoms, amine groups, imine groups, ammonium groups, cyano groups, pyridine groups, pyridinium groups, ether groups, epoxy groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, alkyl groups, aryl groups, arylalkyl groups, alkylaryl groups, silyl groups, siloxyl groups, silane groups, mixtures thereof, and the like;

wherein two or more R groups and/or substituents can be joined together to form a ring.

The R groups can also be a variety of functional groups, including, but not limited to, alcohol (hydroxyl), amine, carboxylic acid, epoxide, fluoroalkyl, halide, imide, acrylate, methacrylate, nitrile, sulfonate, thiol, silanol, oxide, and the like, as well as mixtures thereof. When n is 6, the corresponding structure has $R_1$, $R_2$, $R_3$, $R_4$, $R_5$, and $R_6$ groups as defined hereinabove for when n is 8. When n is 10, the corresponding structure has $R_1$, $R_2$, $R_3$, $R_4$, $R_5$, $R_6$, $R_7$, $R_8$, $R_9$, and $R_{10}$ groups as defined hereinabove for when n is 8. When n is 12, the corresponding structure has R1, $R_1$, $R_2$, $R_3$, $R_4$, $R_5$, $R_6$, $R_7$, $R_8$, $R_9$, and $R_{10}$, $R_{11}$, and $R_{12}$ groups as defined hereinabove for when n is 8. Also included are compounds wherein one or more of the bonds forming the "cage" structure are opened, allowing the silicon and oxygen atoms to have additional substituents thereon, thus:

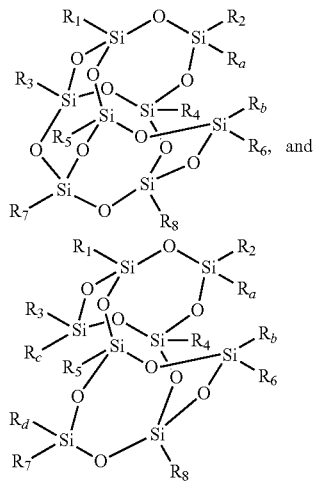

wherein $R_a$, $R_b$, $R_c$, and $R_d$ can have the same definitions as $R_1$ through $R_8$, and can also be substituents, including (but not limited to) imine groups, ammonium groups, cyano groups, pyridine groups, pyridinium groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, azide groups, azo groups, cyanato groups, isocyanato groups, thiocyanato groups, isothiocyanato groups, urethane groups, urea groups, mixtures thereof, and the like, wherein two or more R groups and/or substituents can be joined together to form a ring. Specific examples of compounds of these structures include (but are not limited to) disilanol POSS compounds and tetrasilanol POSS compounds, such as disilanol isobutyl POSS, of the formula

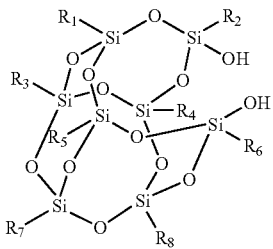

wherein $R_1$, $R_2$, $R_3$, $R_4$, $R_5$, $R_6$, $R_7$, and $R_8$, are all isobutyl, and tetrasilanol phenyl POSS, of the formula

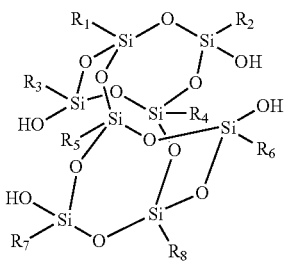

wherein $R_1$, $R_2$, $R_3$, $R_4$, $R_5$, $R_6$, $R_7$, and $R_8$, are all phenyl. Also included are compounds wherein one or more of the silicon atoms and the oxygen atoms bonded thereto are missing, allowing the silicon and oxygen atoms to have additional substituents thereon, thus:

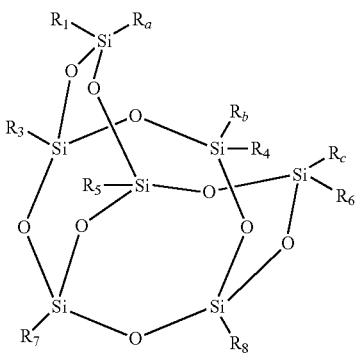

wherein $R_a$, $R_b$, and $R_c$ can have the same definitions as $R_1$ through $R_8$, and can also be substituents, including (but not limited to) hydroxy groups, halogen atoms, amine groups, imine groups, ammonium groups, cyano groups, pyridine groups, pyridinium groups, ether groups, epoxy groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more R groups and/or substituents can be joined together to form a ring. Specific examples of compounds of this structure include (but are not limited to) trisilanol POSS compounds, such as trisilanol phenyl POSS, of the formula

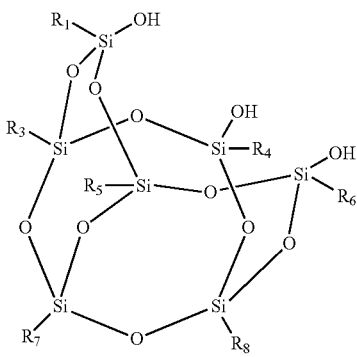

wherein $R_1$, $R_2$, $R_3$, $R_4$, $R_5$, $R_6$, and $R_7$ are all phenyl. Specific examples of suitable R groups include (but are not limited to) phenyl, isobutyl, allyl-bisphenol, cyclopentyl, trimethylsiloxy, methacryl, maleimide, cyclohexyl, and the like.

Specific examples of suitable R groups on the POSS molecules include (but are not limited to) methyl, O—N(CH$_3$)$_{4+}$, ethyl, dibromoethyl, norbornenylethyl, vinyl, trifluoropropyl, chloropropyl, cyanopropyl, mercaptopropyl, aminopropyl, N-methylaminopropyl, propylammonium halide, such as chloride, bromide, iodide, fluoride, and the like, allyl, polyethyleneoxy, of the formula —(CH$_2$CH$_2$(OCH$_2$CH$_2$)$_m$OCH$_3$, wherein m is a number representing the number of repeat OCH$_2$CH$_2$ units, and in one specific embodiment has an average value of about 13.3, isobutyl, cyclopentyl, cyclohexyl, isooctyl, 1-ethyl-3,4-cyclohexanediol, of the formula

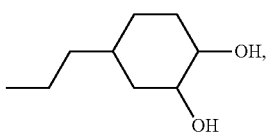

3-hydroxy-3-methylbutyldimethylsiloxyl, of the formula

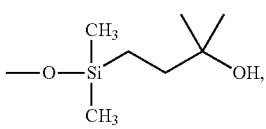

aminoethylaminopropyl, of the formula

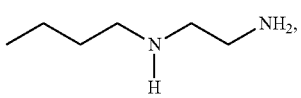

phenyl, chlorobenzyl, chlorobenzylethyl, of the formula

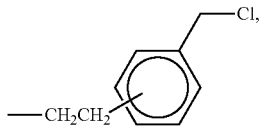

amic acid, of the formula

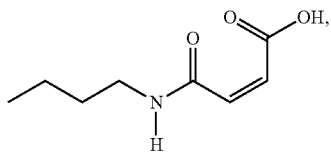

aminophenyl, N-phenylaminopropyl, epoxycyclohexyl, of the formula

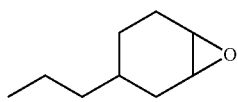

epoxycyclohexyldimethysiloxy, of the formula

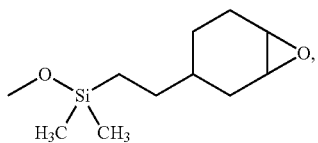

glycidyl, of the formula

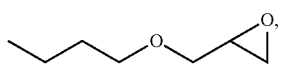

glycidyldimethylsiloxy, of the formula

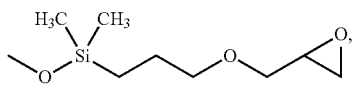

maleimide, of the formula

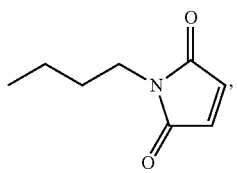

acrylol, of the formula

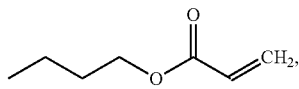

methacryl, of the formula

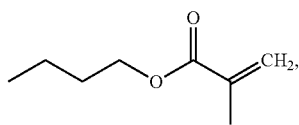

acrylate, of the formula

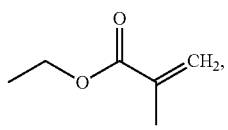

trimethylsiloxyl, of the formula —OSi(CH$_3$)$_3$, norbornenyl, cyclohexenyldimethylsiloxy, of the formula

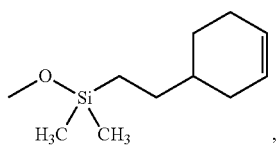

vinyldimethylsiloxy, of the formula

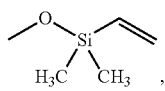

a group of the formula —OSi(CH$_3$)$_2$H, —H, —OH,

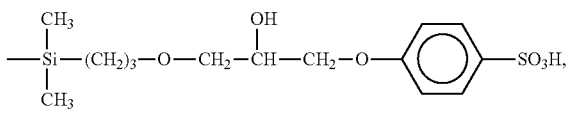

and the like.

In a specific embodiment, the POSS coatings herein comprise a fluoroalkyl-substituted polyhedral oligomeric silsesquioxane. Fluoroalkyl-substituted POSS compounds are thermally and hydrolytically stable and are less hazardous to prepare than other fluorinated compounds. These compounds can also be rendered soluble, which facilitates their incorporation into composite formulations with various polymer systems.

In a specific embodiment wherein the POSS is of the formula

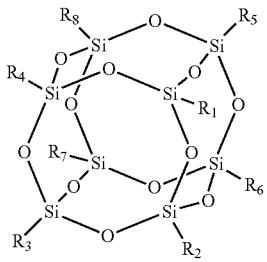

$R_1$, $R_2$, $R_3$, $R_4$, $R_5$, $R_6$, $R_7$, and $R_8$ are each, independently of the other, selected from a fluorine-substituted group comprising (a) alkyl, including linear, branched, saturated, unsaturated, cyclic, acyclic, substituted, and unsubstituted alkyl groups, and wherein hetero atoms in addition to fluorine may optionally be present in the alkyl group; (b) aryl, including substituted and unsubstituted aryl groups, and wherein hetero atoms may optionally be present in the aryl group; (c) arylalkyl, including unsubstituted and substituted arylalkyl groups, wherein the alkyl portion of the arylalkyl group can be linear, branched, saturated, unsaturated, cyclic, or acyclic, and wherein hetero atoms may optionally be present in either or both of the alkyl portion and the aryl portion of the arylalkyl group; (d) alkylaryl, including unsubstituted and substituted alkylaryl groups, wherein the alkyl portion of the alkylaryl group can be linear, branched, saturated, unsaturated, cyclic, or acyclic, and wherein hetero atoms may optionally be present in either or both of the alkyl portion and the aryl portion of the alkylaryl group; (e) siloxyl, including linear, branched, cyclic, acyclic, substituted, and unsubstituted, siloxyl groups, and wherein hetero atoms may optionally be present; (f) silyl, including linear, branched, cyclic, acyclic, substituted, and unsubstituted, silyl groups, and wherein hetero atoms may optionally be present; (g) silane, including linear, branched, cyclic, acyclic, substituted, and unsubstituted, silane groups, and wherein hetero atoms may optionally be present; and (h) a functional group selected from hydroxyl, amine, carboxylic acid, epoxide, fluoroalkyl, halide, imide, acrylate, methacrylate, nitrile, sulfonate, thiol, silanol, and combinations thereof, wherein two or more R groups can be joined together to form a ring;

$R_1$, $R_2$, $R_3$, $R_4$, $R_5$, $R_6$, $R_7$, and $R_8$ are each, independently of the other, selected from a fluorine-substituted group comprising (a) alkyl having from about 1 to about 36 carbon atoms; (b) aryl having from about 6 to about 36 carbon atoms; (c) arylalkyl having from about 6 to about 36 carbon atoms; (d) alkylaryl having from about 6 to about 36 carbon atoms; (e) siloxyl having from about 6 to about 12 silicon atoms; (f) silyl having from about 6 to about 12 silicon atoms; and (g) silane having from about 6 to about 12 silicon atoms;

$R_1$, $R_2$, $R_3$, $R_4$, $R_5$, $R_6$, $R_7$, and $R_8$ are each the same and wherein $R_1$, $R_2$, $R_3$, $R_4$, $R_5$, $R_6$, $R_7$, and $R_8$ are $CH_2CH_2CF_2CF_2CF_2CF_3$;

$CH_2CH_2CF_2CF_2CF_2CF_2CF_2CF_3$; or $CH_2CH_2CF_2CF_2CF_2CF_2CF_2CF_2CF_2CF_3$.

In a specific embodiment, the method herein comprises surface treating carbon black with a POSS compound of the formula:

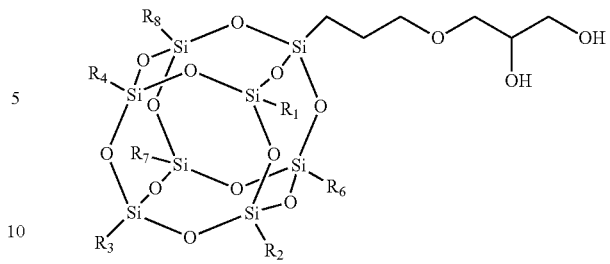

wherein $R_5$ is a diol, in embodiments, 1,2-propanediol isobutyl, $R_1$ through $R_4$ and $R_6$ through $R_8$ are as described above, or, in embodiments, wherein $R_1$ through $R_4$ and $R_6$ through $R_8$ are i-butyl.

In another specific embodiment, the method herein comprises surface treating carbon black with a POSS compound of the formula:

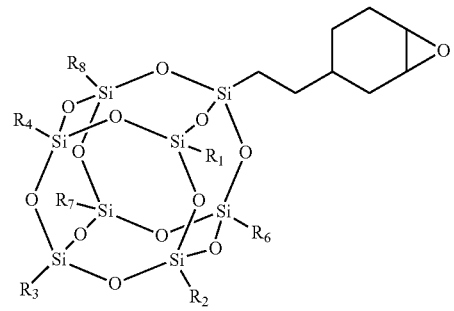

wherein $R_5$ is an epoxy, in embodiments, epoxycyclohexyl isobutyl, $R_1$ through $R_4$ and $R_6$ through $R_8$ are as described above, or, in embodiments, wherein $R_1$ through $R_4$ and $R_6$ through $R_8$ are i-butyl.

In yet another specific embodiment, the method herein comprises surface treating carbon black with a POSS compound of the formula:

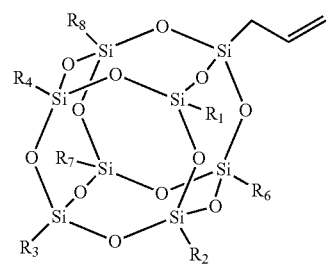

wherein $R_5$ is an allyl, in embodiments, allylisobutyl, $R_1$ through $R_4$ and $R_6$ through $R_8$ are as described above, or, in embodiments, wherein $R_1$ through $R_4$ and $R_6$ through $R_8$ are i-butyl.

The POSS compounds can be prepared by any suitable method. In embodiments, the POSS coatings can be prepared using easy, soft-chemistry synthesis. For example, in embodiments, the POSS compounds can be synthesized via a single-step, base-catalyzed condensation of trialkoxysilanes in alcoholic media, such as

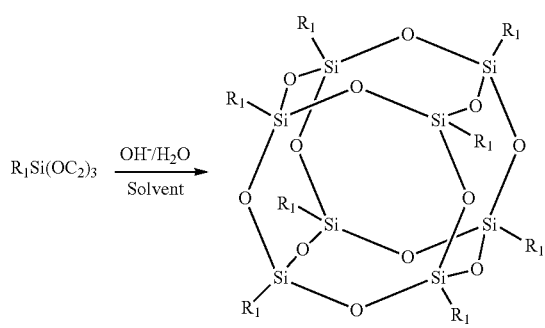

Suitable solvents can be, for example, methyl ethyl ketone, methyl isobutyl ketone, or water. The components can be combined by any suitable method such as standard mixing techniques (stir bar/stir plate) at room temperature as would be known by those of ordinary skill in the art.

This reaction produces nearly quantitative yields of octameric fluoro-substituted POSS compounds, such as 1H,1H,2H,2H-NonaFluorohexyl)$_8$Si$_8$O$_{12}$ (FH) POSS;

(1H,1H,2H,2H-tridecafluorooctyl)$_8$Si$_8$O$_{12}$ (FO) POSS; and (1H,1H,2H,2H-heptadecafluorodecyl)$_8$Si$_8$O$_{12}$ (FD) POSS;

wherein for FH, $R_1$ is $CH_2CH_2CF_2CF_2CF_2CF_3$;

for RO, $R_1$ is $CH_2CH_2CF_2CF_2CF_2CF_2CF_2CF_3$; and for FD, $R_1$ is $CH_2CH_2CF_2CF_2CF_2CF_2CF_2CF_2CF_2CF_3$.

POSS compounds are commercially available from, for example, Hybrid Plastics, Hattiesburg, Miss.

In embodiments, the method herein comprises a method for controlling the percolation threshold of carbon black comprising surface treating carbon black with a polyhedral oligomeric silsesquioxane.

In various embodiments, there is provided a coating composite for imaging components including the POSS surface treated carbon black herein. The coating composite can include a film forming resin and a plurality of POSS surface treated carbon black particles substantially uniformly dispersed in the film forming resin. In embodiments, substantially uniformly dispersed means that the coating is homogeneous. That is, there are no areas depleted of carbon black and no substantially darker areas due to elevated levels of carbon black concentration in the film.

In another embodiment, an imaging component is provided. The imaging component can include a substrate and a coating composite disposed over the substrate, the coating composite including a plurality of POSS surface treated carbon black particles substantially dispersed uniformly in the film forming resin, wherein the coating composite has a surface resistivity in the range of about $10^6$ to about $10^{13}$ Ω/square, and in a specific embodiment, from about $10^8$ to about $10^9$ Ω/square.

In another embodiment, an apparatus for forming an image is provided. The apparatus can include a charging station for uniformly charging a surface of an image receiving member and an imaging station for forming a latent image on the surface of the image receiving member. The apparatus can also include a developing station for converting the latent image to a visible image on the surface of the image receiving member, an intermediate transfer member positioned between the image receiving member and a transfer roller for transferring the developed image from the image receiving member to a media, wherein at least one of the intermediate member and the transfer member can include a coating composite, the coating composite including a plurality of POSS surface treated carbon black particles substantially uniformly dispersed in the film forming resin, wherein the coating composite has a surface resistivity in the range of about $10^6$ to about $10^{13}$ Ω/square, and in a specific embodiment, from about $10^8$ to about $10^9$ Ω/square.

The coating composite for imaging components can include any suitable film forming resin such as polycarbonates, polyesters, polyurethanes, polystyrenes, polyarylethers, polyarylsulfones, polysulfones, polyethersulfones, polyphenylene sulfides, polyvinyl acetate, polyacrylates, polyvinyl acetals, polyamides, polyimides, amino resins, phenolic resins, phenoxy resin, epoxy resins, phenylene oxide resins, polystyrene and acrylonitrile copolymers, vinyl acetate copolymers, acrylate copolymers, alkyd resin, styrene-butadiene copolymers, styrene-alkyd resins, polyvinylcarbazole, and the like. In certain embodiments, the film forming resin can include one or more of acrylic polyol, polyether polyol, and polyester polyol.

In embodiments, the POSS surface treated carbon black particles can be present in the film forming resin composite in an amount of from about 0.01% to about 15%, or from about 0.1% to about 10%, based upon the total weight of the film forming resin composite.

The coating composite can be used for any suitable imaging component of electrostatographic and electrophotographic devices. Exemplary imaging components can include bias charge rolls, bias transfer rolls, magnetic roller sleeves, intermediate transfer belts, and transfer belts.

Imaging apparatus herein can include any suitable apparatus including multi-imaging systems. The apparatus can include an image receiving member and a charging station for uniformly charging a surface of the image receiving member. The image receiving member can include a photoreceptor drum or other imaging member, other electrostatographic imaging receptors such as such as ionographic belts and drums, or electrophotographic belts. The charging station can include any suitable charger such as a corotron, a scorotron, or a bias charger roll. The apparatus can also include an imaging station where an original document can be exposed to a light source for forming a latent image on the image receiving member, an intermediate transfer member positioned between the image receiving member, and a transfer roller for transferring the developed image from the image receiving member to a media. Other members/stations/transfers means can be added or existing members/stations/transfer means can be removed or modified.

In embodiments, an imaging component herein can include a coating composite disposed over a substrate, wherein the coating composite can include a plurality of POSS surface treated carbon black particles substantially uniformly dispersed in a film forming resin, wherein the coating composite has a surface resistivity in the range of about $10^6$ to about $10^{13}$ Ω/square, and in a specific embodiment, from about $10^8$ to about $10^9$ Ω/square. In various embodiments, the substrate of the imaging component can be in the form of at least one of a sheet, a belt, a film, or a cylindrical roll. The substrate can include at least one of polystyrene, acrylic, styrene-acrylic copolymer, styrene-butadiene copolymer, polyamide, polyimide, polyethylene, polyethylene terephthalate, polyethylene naphthalate, polypropylene, polyvinyl alcohol, or vinyl ether resins.

The POSS surface treated carbon black particles can be distributed in the film forming resin of the imaging components by any suitable or desired method, for example, by a physical mixing (that is, non-covalent mixing), and/or a chemical mixing (that is, covalent reaction). In some embodiments, the plurality of POSS surface treated carbon black particles can be incorporated during in-situ processes, such as in-situ crosslinking, in-situ polymerization, and/or in-situ curing processes, of the selected film forming resin. For example, a plurality of POSS surface treated carbon black particles can be dispersed uniformly in a solution of melamine-formaldehyde resins and hydroxylated acrylic resin before the step of coating and curing. In another example, a plurality of POSS surface treated carbon black particles can be dispersed uniformly throughout a polyimide matrix during an in-situ polymerization of the polyimide monomers. In yet another example, a plurality of POSS surface treated carbon black particles can be dispersed throughout an epoxy type polymer matrix during the curing process of the epoxy.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

Comparative Example 1

An untreated carbon black (Vulcan® XC72 carbon black available from Cabot Corporation) was used as a comparative example.

Example 2

Coupling POSS onto a Carbon Black Surface

An amide coupling reaction was performed using 1,2-propanediol isobutyl-POSS (Diol-POSS; available from Hybrid Plastics). A solution of 1.500 grams of Diol-POSS (1.58 millimoles) in $CH_2Cl_2$ was added to a suspension of 15.11 grams of carbon black (Vulcan® XC72 carbon black available from Cabot Corporation), 0.435 gram of dicyclohexylcarbodiimide (DCC; 2.11 millimoles) and 0.266 gram of diisopropylethylamine (DIPEA; 2.06 millimoles) in 200 milliliters of $CH_2Cl_2$. The suspension was sonicated using a Bransonic® Model 2510 ultrasonic cleaner (Branson Ultrasonic Corp.) for 10 minutes prior to the addition of the Diol-POSS solution. After the Diol-POSS was added, the suspension was stirred for 18 hours. The suspension was then centrifuged to isolate the particles, which were washed with copious amounts of $CH_2Cl_2$. The sample was then dried in vacuo.

Example 3

Coupling POSS onto a Carbon Black Surface

An epoxy coupling reaction was performed using epoxycyclohexyl isobutyl-POSS (Epoxy-POSS available from Hybrid Plastics). A suspension of 10.82 grams of Vulcan® XC72 carbon black in 109.92 grams of dimethylformamide (DMF) was added to a solution of 0.988 grams of Epoxy-POSS (1.05 millimoles) in DMF and sonicated using a Bransonic® Model 2510 ultrasonic cleaner for 10 minutes. After sonication, the suspension was stirred and 1 milliliter of HCl was added. The suspension was then heated to reflux and stirred for 18 hours. The suspension was then cooled to room temperature and centrifuged to isolate the particles. The solvent was decanted and the particles were washed with acetone. The sample was then dried in vacuo.

Example 4

Coupling POSS onto a Carbon Black Surface

Carbon black was treated using allylisobutyl-POSS (Allyl-POSS available from Hybrid Plastics). A suspension of 10.36 grams of Vulcan® XC72 carbon black, 100.33 grams of dodecane and 1.058 grams of Allyl-POSS (1.23 millimoles) was sonicated using a Bransonic® Model 2510 ultrasonic cleaner for 10 minutes. Following sonication, the suspension was heated to reflux and stirred for 18 hours. The suspension was then cooled to room temperature and centrifuged to isolate the particles. The particles were then washed with hexanes and the solid was dried in vacuo.

Comparative Example 5

MWCNTs available from Nanostructured & Amorphous Materials Inc.; 20-40 nanometers diameter, 1-2 micrometer length, 40-600 $m^2/g$ were used as a comparative example.

Examples 1-4 were examined by X-Ray Photoelectron Spectroscopy (XPS) to determine the coupling efficiency based on the Si atomic percentage (At %) found on the surface of the carbon blacks. The XPS results are shown in Table 1.

TABLE 1

| Example | Type of Carbon Black | At % C | At % O | At % Si |
| --- | --- | --- | --- | --- |
| Comparative Example 1 | Untreated Vulcan ® XC72 | 98.9 | 1.1 | 0 |
| Example 2 | Diol-POSS treated Vulcan ® XC72 | 99.2 | 0.7 | 0.1 |
| Example 3 | Epoxy-POSS treated Vulcan ® XC72 | 98.6 | 1.2 | 0.2 |
| Example 4 | Allyl-POSS treated Vulcan ® XC72 | 98 | 1.6 | 0.5 |

The epoxy-POSS surface treated carbon black of Example 3 was analyzed to determine carbon black conductivity.

Films of the material of Example 3 were prepared by ball milling the carbon black at various concentrations in a 50:50 mixture (by total solid mass) of Cymel® 323 melamine (Cytec Industries Inc.) and Paraloid® AT-410 (Rohm & Haas) in methyl ethyl ketone. To each sample was added about 80 grams of ⅛" stainless steel shot and roll milled over the course of 3 days. The samples were then filtered through a cotton-tip filter to remove the shot from the dispersion.

As a control, similar samples were prepared with the untreated carbon black of Comparative Example 1. In addition, similar dispersions were prepared using multi-walled carbon nanotubes of Comparative Example 5.

Each of the dispersions was subsequently coated on a polyethylene terephthalate (PET) substrate using a 0.002" bird bar. The films were dried in a convection oven for 10 minutes at 140° C. resulting in about 20 micrometer films. Surface resistivity was measured using a Hiresta UP Resistivity Meter with a supply voltage of 10 V. Resistivity measurements for the untreated carbon black of Comparative Example 1, the POSS-treated carbon black of Examples 2-4, and MWCNTs of Comparative Example 5 are shown in FIG. 1.

In FIG. 1, it can be seen that there is a shift in the percolation threshold of the POSS-treated carbon black compared to that of the untreated carbon black. Resistivities for the POSS-treated carbon black down to 2 wt % carbon black in the film were obtained, whereas the resistivity of the untreated carbon black was outside the region of measure (>10$^{14}$ Ω/square) below 3 wt % untreated carbon black. Further, the plot of the POSS-treated carbon black is comparable to that of the MWCNTs in terms of the location of the percolation threshold. The data in Table 2 emphasizes the results seen in this graph.

TABLE 2

| Weight % Carbon Black | Average Surface Resistivity (Ω/square) | Weight % MWCNT | Average Surface Resistivity (Ω/square) | Weight % POSS-Carbon Black | Average Surface Resistivity (Ω/square) |
|---|---|---|---|---|---|
| — | — | — | — | 0.5 | OVER* |
| 1.0 | OVER* | 1.0 | OVER* | 1.0 | OVER* |
| — | — | — | — | 1.5 | OVER* |
| 2.0 | OVER* | 2.0 | $4.04 \times 10^9$ | 2.0 | $2.52 \times 10^8$ |
| 2.4 | OVER* | — | — | 2.5 | $6.93 \times 10^7$ |
| 3.0 | $5.18 \times 10^7$ | 3.0 | $2.88 \times 10^8$ | 3.0 | $5.58 \times 10^7$ |
| 4.0 | $5.94 \times 10^6$ | 4.0 | $3.02 \times 10^7$ | 4.0 | $1.79 \times 10^7$ |
| 5.1 | $2.3 \times 10^6$ | 4.9 | $9.63 \times 10^6$ | 5.1 | $3.9 \times 10^6$ |

*OVER indicates that the resistivity could not be measured by the Hiresta UP Resistivity Meter (>10$^{14}$ Ω/square)

In embodiments, the conductivity of carbon black is tailored by the present surface treatment method wherein the carbon black particles are treated with various derivatives of POSS. The POSS-treated carbon black particles can be prepared using different reaction methodologies. In coupling POSS to the surface of carbon black, the percolation threshold can be shifted to lower loadings of the particles compared to untreated carbon black. The location of this percolation curve makes the POSS-treated particles resemble that of carbon nanotubes more so than the percolation threshold of untreated carbon black.

A method for shifting the percolation threshold of carbon black is described comprising surface treatment of carbon black with polyhedral oligomeric silsesquioxane (POSS). In a variety of applications, carbon black can be used to achieve a certain desired conductivity level. A subtle change in the carbon black concentration can result in a large change in the resistivity due to the percolation threshold. By controlling the amount of POSS used in the surface treatment of the carbon black, a desired conductivity level can be achieved. The method herein, therefore, can be described as tuning the conductivity of carbon black. The disclosure herein describes, in embodiments, various derivatives of POSS, including diol, epoxy, and allyl. The chemical structure and the preparation methods are further described. Each of the reactions yields different levels of POSS coupling with the carbon black. Resistivity measurements performed on a thin film of epoxy-POSS treated carbon black show that the resistivity is lower for treated carbon black than for untreated carbon black and, in embodiments, is at the same level as multi-walled carbon nanotubes while being less expensive than carbon nanotubes. In embodiments, the method and POSS surface treated carbon black enables achievement of desired resistivity measurements with lower loadings of carbon black than previously required. The method can be used in a variety of applications, including, but not limited to, applications employing conductive materials and for other industries. In embodiments, the method can be used to prepare materials for xerographic components and technology, intermediate transfer belts, biased charging rolls, inks, toners and carriers.

In embodiments, various reactions can be performed to couple POSS onto the carbon black surface. When prepared as a film, the POSS-treated carbon black gives a resistivity in the range of 10$^8$-10$^9$ Ω/square when the particles composition comprises 2.0 weight % of the film. This is substantially different than untreated carbon black, in which the resistivity is greater than 10$^{14}$ Ω/square with carbon black concentrations less than 3 weight % based on the total weight of the film. The resistivity profile of POSS-treated carbon black can resemble that of carbon nanotubes, in which the materials do not become resistive until a substantially small concentration of the particles are present in the film (<2 weight %, based on the total weight of the film).

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

The invention claimed is:

1. A method for treating a carbon allotrope comprising:
providing a carbon allotrope selected from the group consisting of carbon black, amorphous carbon, glassy carbon, graphite, graphene, fullerenes, or a mixture thereof; and
surface treating the carbon allotrope by coupling the carbon allotrope with a polyhedral oligomeric silsesquioxane, wherein the polyhedral oligomeric silsesquioxane comprises a compound of the formula

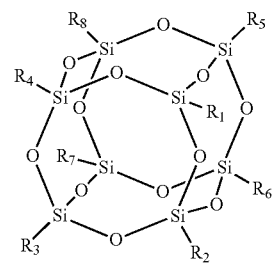

wherein $R_1$, $R_2$, $R_3$, $R_4$, $R_6$, $R_7$, and $R_8$ are each, independently of the other, selected from the group consisting of:
(a) alkyl, including linear, branched, saturated, unsaturated, cyclic, acyclic, substituted, and unsubstituted alkyl groups, and wherein hetero atoms may optionally be present in the alkyl group;
(b) aryl, including substituted and unsubstituted aryl groups, and wherein hetero atoms may optionally be present in the aryl group;
(c) arylalkyl, including unsubstituted and substituted arylalkyl groups, wherein the alkyl portion of the arylalkyl group can be linear, branched, saturated, unsaturated, cyclic, or acyclic, and wherein hetero atoms may optionally be present in either or both of the alkyl portion and the aryl portion of the arylalkyl group;

(d) alkylaryl, including unsubstituted and substituted alkylaryl groups, wherein the alkyl portion of the alkylaryl group can be linear, branched, saturated, unsaturated, cyclic, or acyclic, and wherein hetero atoms may optionally be present in either or both of the alkyl portion and the aryl portion of the alkylaryl group;

(e) siloxyl, including linear, branched, cyclic, acyclic, substituted, and unsubstituted, siloxyl groups, and wherein hetero atoms may optionally be present;

(f) silyl, including linear, branched, cyclic, acyclic, substituted, and unsubstituted, silyl groups, and wherein hetero atoms may optionally be present;

and wherein $R_5$ is selected from the group consisting of hydrogen, hydroxyl, amine, carboxylic acid, epoxide, halide, imide, acrylate, methacrylate, nitrile, sulfonate, thiol, silanol, dibromoethyl, norbornenylethyl, vinyl, chloropropyl, cyanopropyl, mercaptopropyl, aminopropyl, N-methylaminopropyl, propylammonium halide, allyl, chlorobenzyl, aminophenyl, N-phenylaminopropyl, norbornenyl, a group of the formula —$(CH_2CH_2(OCH_2CH_2)_mOCH_3$, wherein m is a number representing the number of repeat $OCH_2CH_2$ units, a group of the formula O—$N^+(CH_3)_4$,

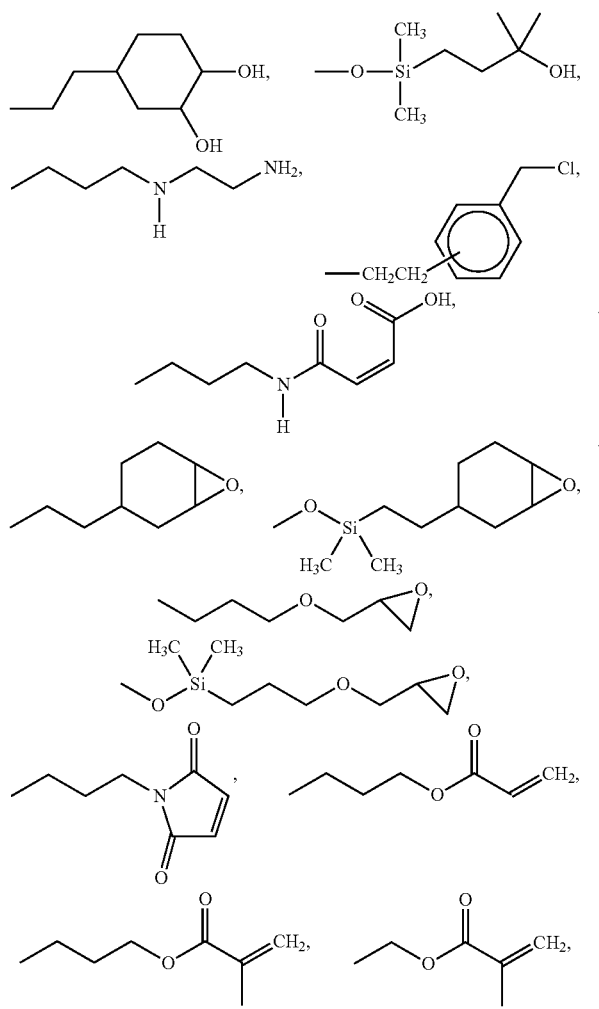

and combinations thereof.

2. The method of claim 1, wherein the carbon allotrope is carbon black; and
wherein surface treating carbon black comprises controlling a percolation threshold of carbon black by coupling of carbon black with a polyhedral oligomeric silsesquioxane.

3. The method of claim 1, wherein the carbon allotrope is carbon black; and
wherein surface treating carbon black comprises controlling a percolation threshold of carbon black by coupling of carbon black with a polyhedral oligomeric silsesquioxane such that the percolation threshold of the carbon black is reduced from a percolation threshold of about 3 weight percent for untreated carbon black to a percolation threshold of about 2 weight percent for POSS surface treated carbon black.

4. The method of claim 1, wherein the carbon allotrope is carbon black; and
wherein surface treating carbon black comprises coupling carbon black with a polyhedral oligomeric silsesquioxane to enhance the conductivity of carbon black at low loading levels.

5. A film comprising a carbon allotrope prepared with the method of claim 1, wherein the carbon allotrope is carbon black; and
wherein the film has a loading level of 2 weight % POSS surface treated carbon black and provides a resistivity of $10^8$ Ω/square.

6. The film of claim 5,
wherein the film comprising the surface treated carbon black has a surface resistivity of about $10^6$ to about $10^{13}$ Ω/square.

7. The film of claim 5,
wherein the film having the surface treated carbon black has a surface resistivity of about $10^8$ to about $10^9$ Ω/square.

8. The film of claim 5,
wherein the film having the surface treated carbon black has a conductivity profile that is the same as or similar to multi-walled carbon nanotubes.

9. The method of claim 1, wherein the carbon allotrope is carbon black; and
wherein surface treating comprises:
preparing a solution comprising POSS and a liquid;
contacting the POSS solution with a suspension comprising carbon black, a coupling agent, and a base.

10. The method of claim 9, wherein the liquid comprises a halogenated organic solvent;
   wherein the coupling agent is selected from the group consisting of carbodiimides, triazoles, or a mixture or combination thereof; and
   wherein the base is selected from the group consisting of piperidine, piperizine, 1-hydroxypiperidine, tetrabutylammonium fluoride, 1,8-diazabicyclo[5.4.0]undec-7-ene, diisopropylethylamine (DIPEA), or a mixture or combination thereof.

11. The method of claim 1, wherein the carbon allotrope is carbon black; and
   wherein the polyhedral oligomeric silsesquioxane comprises a compound of the formula

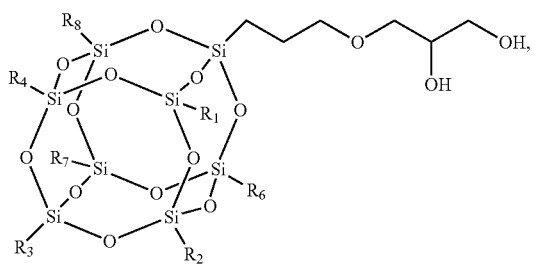

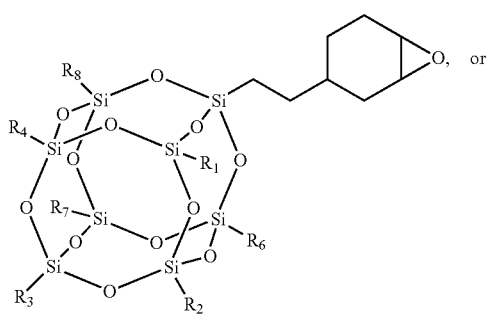

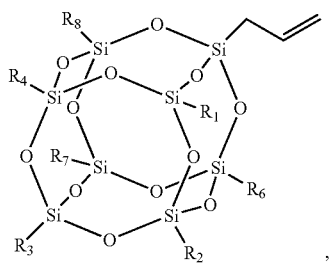

wherein $R_1$ through $R_4$ and $R_6$ through $R_8$ are as defined in claim 1.

12. A surface treated carbon allotrope comprising:
   a carbon allotrope selected from the group consisting of carbon black, amorphous carbon, glassy carbon, graphite, graphene, fullerenes, or a mixture thereof, having a polyhedral oligomeric silsesquioxane coupled to the surface of the carbon allotrope, wherein the polyhedral oligomeric silsesquioxane comprises a compound of the formula

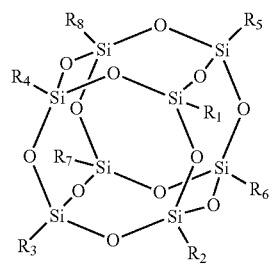

wherein $R_1$, $R_2$, $R_3$, $R_4$, $R_6$, $R_7$, and $R_8$ are each, independently of the other, selected from the group consisting of:
(a) alkyl, including linear, branched, saturated, unsaturated, cyclic, acyclic, substituted, and unsubstituted alkyl groups, and wherein hetero atoms may optionally be present in the alkyl group;
(b) aryl, including substituted and unsubstituted aryl groups, and wherein hetero atoms may optionally be present in the aryl group;
(c) arylalkyl, including unsubstituted and substituted arylalkyl groups, wherein the alkyl portion of the arylalkyl group can be linear, branched, saturated, unsaturated, cyclic, or acyclic, and wherein hetero atoms may optionally be present in either or both of the alkyl portion and the aryl portion of the arylalkyl group;
(d) alkylaryl, including unsubstituted and substituted alkylaryl groups, wherein the alkyl portion of the alkylaryl group can be linear, branched, saturated, unsaturated, cyclic, or acyclic, and wherein hetero atoms may optionally be present in either or both of the alkyl portion and the aryl portion of the alkylaryl group;
(e) siloxyl, including linear, branched, cyclic, acyclic, substituted, and unsubstituted, siloxyl groups, and wherein hetero atoms may optionally be present;
(f) silyl, including linear, branched, cyclic, acyclic, substituted, and unsubstituted, silyl groups, and wherein hetero atoms may optionally be present;
and
wherein $R_5$ is selected from the group consisting of hydrogen, hydroxyl, amine, carboxylic acid, epoxide, halide, imide, acrylate, methacrylate, nitrile, sulfonate, thiol, silanol, dibromoethyl, norbornenylethyl, vinyl, chloropropyl, cyanopropyl, mercaptopropyl, aminopropyl, N-methylaminopropyl, propylammonium halide, allyl, chlorobenzyl, aminophenyl, N-phenylaminopropyl, norbornenyl, a group of the formula —(CH$_2$CH$_2$(OCH$_2$CH$_2$)$_m$OCH$_3$, wherein m is a number representing the number of repeat OCH$_2$CH$_2$ units, a group of the formula O—N$^+$(CH$_3$)$_4$,

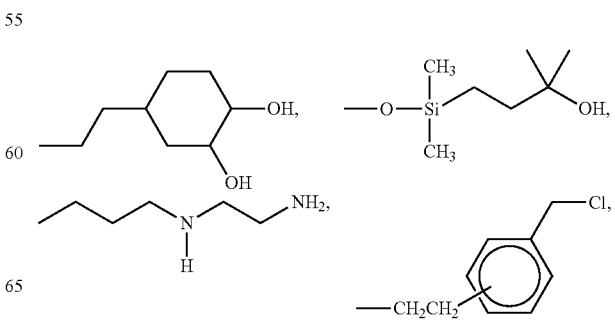

-continued

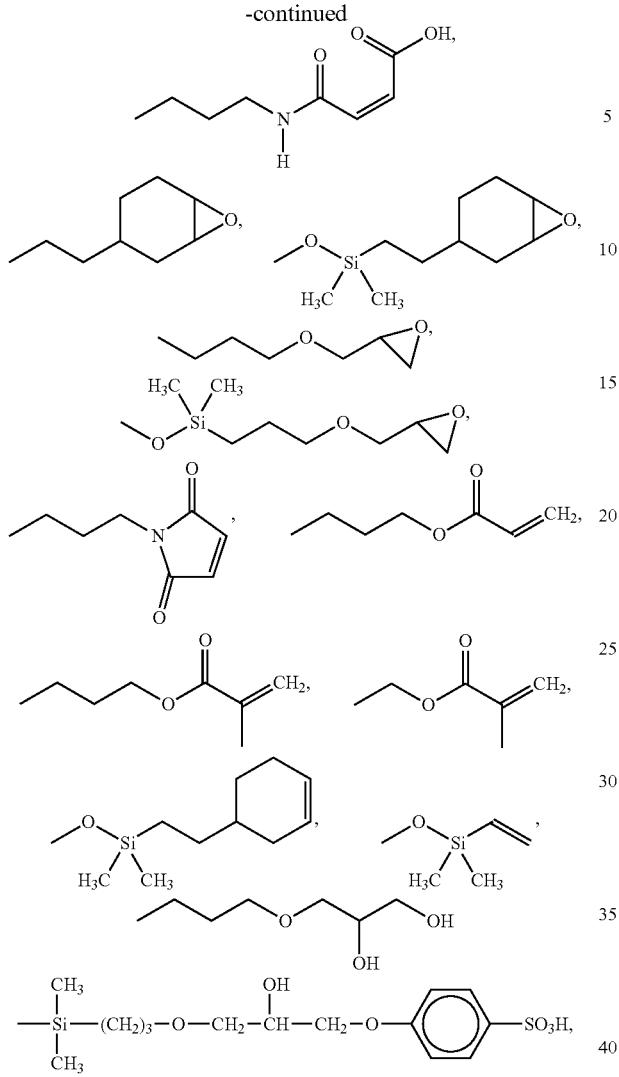

and combinations thereof.

13. A film comprising the surface treated carbon allotrope of claim 12, wherein the carbon allotrope is carbon black; and
wherein the film having the surface treated carbon black has a surface resistivity of about $10^8$ to about $10^9$ Ω/square.

14. The surface treated carbon black of claim 12, wherein the carbon allotrope is carbon black; and
wherein the polyhedral oligomeric silsesquioxane comprises a compound of the formula

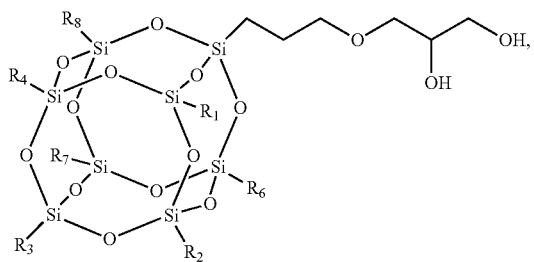

-continued

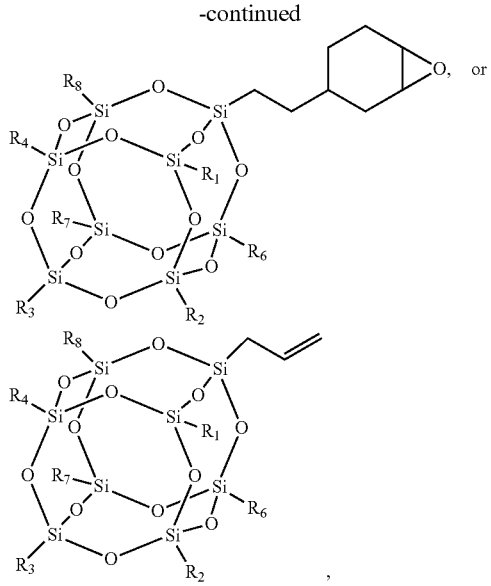

wherein $R_1$ through $R_4$ and $R_6$ through $R_8$ are as defined in claim 12.

15. A coating composite for imaging components comprising:
a film forming resin; and
polyhedral oligomeric silsesquioxane surface treated carbon allotrope substantially uniformly dispersed in the film forming resin, wherein the carbon allotrope is selected from the group consisting of carbon black, amorphous carbon, glassy carbon, graphite, graphene, fullerenes, or a mixture thereof, and wherein the polyhedral oligomeric silsesquioxane comprises a compound of the formula

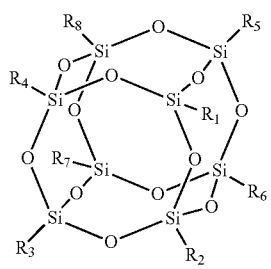

wherein $R_1$, $R_2$, $R_3$, $R_4$, $R_6$, $R_7$, and $R_8$ are each, independently of the other, selected from the group consisting of:
(a) alkyl, including linear, branched, saturated, unsaturated, cyclic, acyclic, substituted, and unsubstituted alkyl groups, and wherein hetero atoms may optionally be present in the alkyl group;
(b) aryl, including substituted and unsubstituted aryl groups, and wherein hetero atoms may optionally be present in the aryl group;
(c) arylalkyl, including unsubstituted and substituted arylalkyl groups, wherein the alkyl portion of the arylalkyl group can be linear, branched, saturated, unsaturated, cyclic, or acyclic, and wherein hetero atoms may optionally be present in either or both of the alkyl portion and the aryl portion of the arylalkyl group;

(d) alkylaryl, including unsubstituted and substituted alkylaryl groups, wherein the alkyl portion of the alkylaryl group can be linear, branched, saturated, unsaturated, cyclic, or acyclic, and wherein hetero atoms may optionally be present in either or both of the alkyl portion and the aryl portion of the alkylaryl group;

(e) siloxyl, including linear, branched, cyclic, acyclic, substituted, and unsubstituted, siloxyl groups, and wherein hetero atoms may optionally be present;

(f) silyl, including linear, branched, cyclic, acyclic, substituted, and unsubstituted, silyl groups, and wherein hetero atoms may optionally be present;

and wherein $R_5$ is selected from the group consisting of hydrogen, hydroxyl, amine, carboxylic acid, epoxide, halide, imide, acrylate, methacrylate, nitrile, sulfonate, thiol, silanol, dibromoethyl, norbornenylethyl, vinyl, chloropropyl, cyanopropyl, mercaptopropyl, aminopropyl, N-methylaminopropyl, propylammonium halide, allyl, chlorobenzyl, aminophenyl, N-phenylaminopropyl, norbornenyl, a group of the formula —(CH$_2$CH$_2$(OCH$_2$CH$_2$)$_m$OCH$_3$, wherein m is a number representing the number of repeat OCH$_2$CH$_2$ units, a group of the formula O—N$^+$(CH$_3$)$_4$,

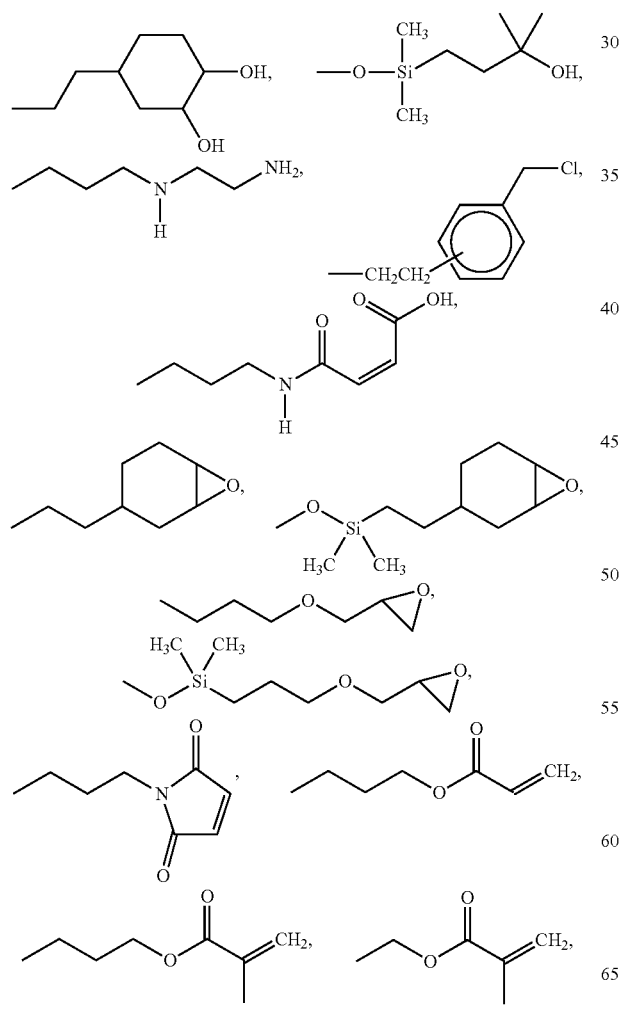

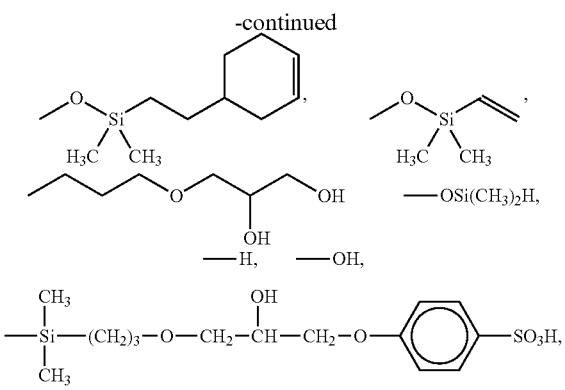

and combinations thereof.

16. The coating composite of claim 15, wherein the carbon allotrope is carbon black; and wherein the coating composite has a surface resistivity of about $10^8$ to about $10^9$ Ω/square.

17. The coating composite of claim 15, wherein the carbon allotrope is carbon black; and wherein the polyhedral oligomeric silsesquioxane comprises a compound of the formula

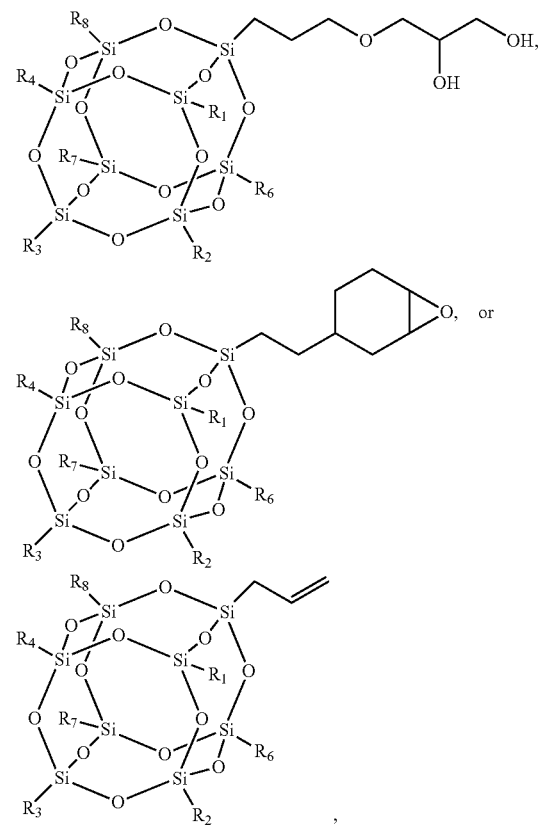

wherein $R_1$ through $R_4$ and $R_6$ through $R_8$ are as defined in claim 15.

18. An imaging component comprising:

a substrate;

a coating composite disposed over the substrate, the coating composite comprising polyhedral oligomeric silsesquioxane surface treated carbon allotrope substantially uniformly dispersed in a film forming resin, wherein the carbon allotrope is selected from the group consisting of carbon black, amorphous carbon, glassy carbon, graphite, graphene, fullerenes, or a mixture thereof, and wherein the polyhedral oligomeric silsesquioxane comprises a compound of the formula

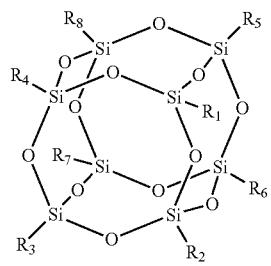

wherein $R_1$, $R_2$, $R_3$, $R_4$, $R_6$, $R_7$, and $R_8$ are each, independently of the other, selected from the group consisting of:

(a) alkyl, including linear, branched, saturated, unsaturated, cyclic, acyclic, substituted, and unsubstituted alkyl groups, and wherein hetero atoms may optionally be present in the alkyl group;

(b) aryl, including substituted and unsubstituted aryl groups, and wherein hetero atoms may optionally be present in the aryl group;

(c) arylalkyl, including unsubstituted and substituted arylalkyl groups, wherein the alkyl portion of the arylalkyl group can be linear, branched, saturated, unsaturated, cyclic, or acyclic, and wherein hetero atoms may optionally be present in either or both of the alkyl portion and the aryl portion of the arylalkyl group;

(d) alkylaryl, including unsubstituted and substituted alkylaryl groups, wherein the alkyl portion of the alkylaryl group can be linear, branched, saturated, unsaturated, cyclic, or acyclic, and wherein hetero atoms may optionally be present in either or both of the alkyl portion and the aryl portion of the alkylaryl group;

(e) siloxyl, including linear, branched, cyclic, acyclic, substituted, and unsubstituted, siloxyl groups, and wherein hetero atoms may optionally be present;

(f) silyl, including linear, branched, cyclic, acyclic, substituted, and unsubstituted, silyl groups, and wherein hetero atoms may optionally be present;

and wherein $R_5$ is selected from the group consisting of hydrogen, hydroxyl, amine, carboxylic acid, epoxide, halide, imide, acrylate, methacrylate, nitrile, sulfonate, thiol, silanol, dibromoethyl, norbornenylethyl, vinyl, chloropropyl, cyanopropyl, mercaptopropyl, aminopropyl, N-methylaminopropyl, propylammonium halide, allyl, chlorobenzyl, aminophenyl, N-phenylaminopropyl, norbornenyl, a group of the form —$(CH_2CH_2(OCH_2CH_2)_mOCH_3$, wherein m is a number representing the number of $OCH_2CH_2$ units, a group of the formula O—$N^+(CH_3)_4$,

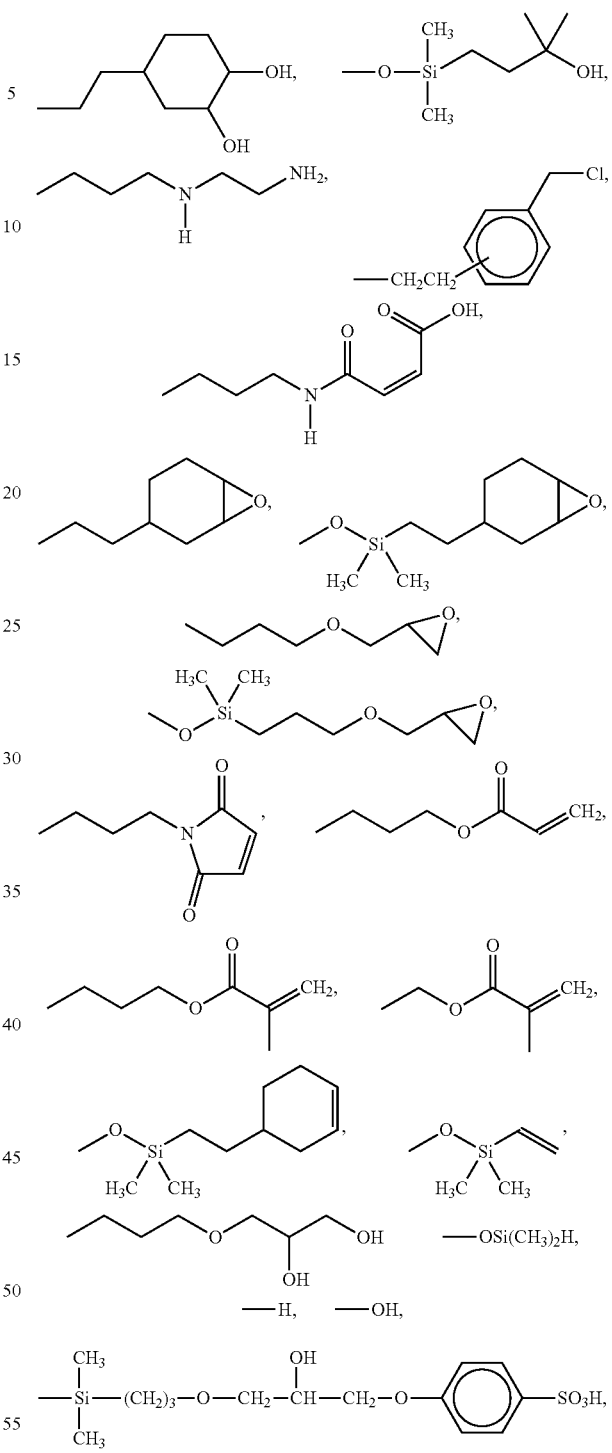

and combinations thereof;

wherein the coating composite has a surface resistivity of about $10^8$ to about $10^9$ Ω/square.

19. The imaging component of claim 18, wherein the carbon allotrope is carbon black; and wherein the polyhedral oligomeric silsesquioxane comprises a compound of the formula

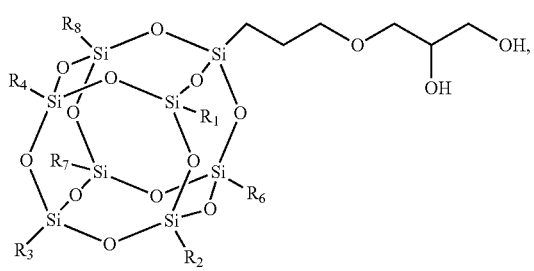
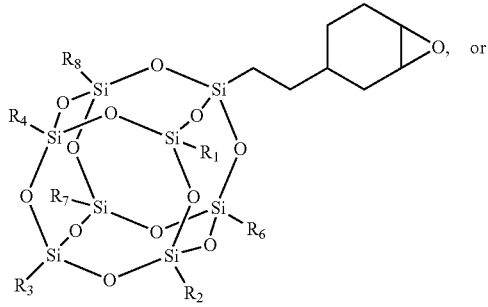
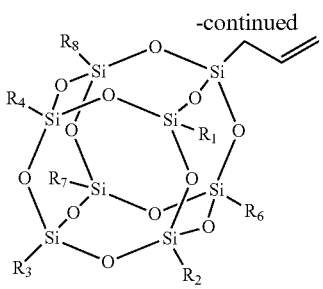
wherein $R_1$ through $R_4$ and $R_6$ through $R_8$ are as defined in claim 18.
20. The imaging component of claim 18, wherein the carbon allotrope is carbon black; and
wherein the coating composite has a surface resistivity of about $10^8$ to about $10^9$ Ω/square.
* * * * *